United States Patent
Al-Zaqri et al.

(10) Patent No.: US 10,016,752 B1
(45) Date of Patent: Jul. 10, 2018

(54) METHOD OF MAKING PALLADIUM NANOPARTICLES

(71) Applicant: KING SAUD UNIVERSITY, Riyadh (SA)

(72) Inventors: Nabil Ahmed Al-Zaqri, Riyadh (SA); Ismail Khalil Warad, Riyadh (SA); Ali Mohammed Alsalme, Riyadh (SA); Mujeeb Abdullah Sultan, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/715,008

(22) Filed: Sep. 25, 2017

(51) Int. Cl.
*B01J 37/34* (2006.01)
*B01J 19/12* (2006.01)
(Continued)

(52) U.S. Cl.
CPC ............ *B01J 37/346* (2013.01); *B01J 19/126* (2013.01); *B01J 23/44* (2013.01); *B01J 35/0013* (2013.01); *B01J 37/04* (2013.01); *C07F 15/006* (2013.01)

(58) Field of Classification Search
CPC ........ B01J 12/126; B01J 37/346; B01J 23/44; B01J 19/126; B01J 35/0013; B01J 37/04; C07F 15/006
(Continued)

(56) References Cited

U.S. PATENT DOCUMENTS 8,114,807 B2   2/2012   Porter et al.
8,741,036 B2   6/2014   Wu
(Continued)

FOREIGN PATENT DOCUMENTS

CN   101480612 A   7/2009
CN   106512993 A   3/2017
(Continued)

OTHER PUBLICATIONS

Galletti et al, "An easy microwave-assisted process for the synthesis of nanostructured palladium catalysts and their use in the selective hydrogenation of cinnamaldehyde," Applied Catalysis A: General 386 (2010) pp. 124-131 (Year: 2010).*
(Continued)

*Primary Examiner* — Ibrahime A Abraham
*Assistant Examiner* — Colleen M Raphael
(74) *Attorney, Agent, or Firm* — Richard C. Litman

(57) ABSTRACT

The method of making palladium nanoparticles is a microwave thermolysis-based method of making palladium nanoparticles from a complex of palladium(II) acetate $Pd(O_2CCH_3)_2$ (or $Pd(OAc)_2$) and a ligand. The complex of palladium(II) acetate and the ligand is melted in oleic acid and dichloromethane to form a solution. The ligand is 1-(pyridin-2-yldiazenyl)naphthalen-2-ol ($C_{15}H_{11}N_3O$), which has the structure:

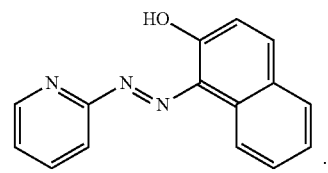

The solution is stirred for two hours under an inert argon atmosphere, and then irradiated with microwave radiation to produce palladium nanoparticles.

3 Claims, 10 Drawing Sheets

(51) Int. Cl.
  *B01J 37/04* (2006.01)
  *B01J 35/00* (2006.01)
  *B01J 23/44* (2006.01)
  *C07F 15/00* (2006.01)

(58) Field of Classification Search
  USPC .................................................. 204/157.43
  See application file for complete search history.

(56) References Cited

U.S. PATENT DOCUMENTS

| | | |
|---|---|---|
| 8,741,037 B2 | 6/2014 | Wu |
| 8,940,197 B2 | 1/2015 | Liu et al. |
| 8,962,512 B1* | 2/2015 | Burton ................ B01J 21/18 502/185 |
| 2007/0207335 A1* | 9/2007 | Karandikar ............ B32B 15/01 428/560 |
| 2013/0200312 A1* | 8/2013 | Wu ....................... C09D 11/52 252/514 |
| 2013/0211106 A1* | 8/2013 | El-Shall ............... B01J 19/126 549/445 |
| 2015/0129813 A1* | 5/2015 | Peng ....................... B22F 9/24 252/514 |
| 2015/0212059 A1* | 7/2015 | Schechter .......... G01N 33/1813 436/79 |
| 2017/0007986 A9 | 1/2017 | Drzal et al. |

FOREIGN PATENT DOCUMENTS

| | | | |
|---|---|---|---|
| JP | 2011-214142 A | 10/2011 | |
| WO | WO-2013048270 A1 * | 4/2013 | ......... C23C 14/0605 |

OTHER PUBLICATIONS

Hadar et al, "Detection of heavy metals in water using dye nano-complexants and a polymeric film," J. of Hazardous Materials 260 (2013) pp. 652-659 (Year: 2013).*

Abdelsayed et al. "Microwave Synthesis of Bimetallic Nanoalloys and CO Oxidation on Ceria-Supported Nanoalloys," Chemistry of Materials, 21.13 (2009): 2825-2834.

* cited by examiner

METHOD OF MAKING PALLADIUM NANOPARTICLES

BACKGROUND

1. Field

The disclosure of the present patent application relates to the manufacture of palladium nanoparticles, and particularly to a microwave thermolysis-based method of making palladium nanoparticles.

2. Description of the Related Art

Palladium is a versatile metal with a wide range of applications. Palladium is commonly found in catalytic converters, which convert as much as 90% of the harmful gases in automobile exhaust (hydrocarbons, carbon monoxide and nitrogen dioxide) into less noxious substances (nitrogen, carbon dioxide and water vapor). Palladium is also used in electronics, dentistry, medicine, hydrogen purification, chemical applications, groundwater treatment and jewelry. Palladium is a key component of fuel cells, which react hydrogen with oxygen to produce electricity, heat, and water.

There is presently a great interest in nano-scale structures formed from palladium, particularly in the fields polymers, printing inks, coatings, micro-electronics and medicine. The production of palladium nanoparticles is commonly performed via thermal decomposition, reduction of salts, radioactive methods, technical emulsifying flour, laser diffraction and thermal melting. These methods, however, are typically not efficient when applied on an industrial scale; i.e., in order to effectively and efficiently produce palladium nanoparticles with these techniques, the various methods must be applied under highly controlled laboratory conditions. Using these present techniques to produce nanoparticles of palladium on an industrial scale would be extremely costly and difficult. Thus, a method of making palladium nanoparticles solving the aforementioned problems is desired.

SUMMARY

The method of making palladium nanoparticles includes forming a complex of palladium(II) acetate $Pd(O_2CCH_3)_2$ (or $Pd(OAc)_2$) and a ligand. The complex of palladium(II) acetate and the ligand can be melted in oleic acid and dichloromethane to form a solution. The solution can be stirred for about two hours under an inert argon atmosphere, and then irradiated with microwave radiation to produce palladium nanoparticles. The ligand is 1-(pyridin-2-yldiazenyl)naphthalen-2-ol ($C_{15}H_{11}N_3O$) (referred to herein as "the diazo pigment ligand"), which has the structure:

These and other features of the present invention will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

A method of making palladium nanoparticles includes use of a metal complex to form nano-palladium or palladium nanoparticles. The method can include synthesizing palladium nanoparticles from a complex of palladium(II) acetate $Pd(O_2CCH_3)_2$ (or $Pd(OAc)_2$) and a ligand. The complex of palladium(II) acetate and ligand can be melted in oleic acid and dichloromethane to form a solution. The solution can be exposed to microwave radiation to form the palladium nanoparticles. The ligand can be 1-(pyridin-2-yldiazenyl)naphthalen-2-ol ($C_{15}H_{11}N_3O$), (also referred to herein as the "diazo pigment ligand") which has the following structure:

In an exemplary embodiment, the complex of palladium (II) acetate and the diazo pigment ligand, can be prepared by melting about 0.05 g (0.24 mmol) of palladium(II) acetate in a flask and then dissolving the palladium(II) acetate in about 20 mL of dichloromethane to form a solution. The solution can be kept at a temperature of about 80° C. for about 30 minutes under a flow of argon. The solution can be treated dropwise with about 0.06 g (0.236 mmol) of the diazo pigment ligand dissolved in about 20 mL of dichloromethane to provide a dark green solution including the complex of palladium(II) acetate and the diazo pigment ligand.

In an exemplary embodiment, about 0.2 g of the complex of palladium(II) acetate and the diazo pigment ligand can be melted in about 5 mL of oleic acid and about 1 mL of dichloromethane to ensure melting. This solution can be stirred for about two hours under an inert argon atmosphere. The solution can then be exposed to microwave radiation to provide the palladium nanoparticles. The palladium nanoparticles can be about 2 nm to about 10 nm in diameter, e.g., about 4.1 nm to about 5.75 nm or about 6 nm to about 8 nm. The palladium nanoparticles can be crystalline. The palladium nanoparticles can be generally spherical in shape.

In experiments, 0.2 g of the complex of palladium(II) acetate and the diazo pigment ligand were melted in 5 mL of oleic acid, with 1 mL of the dichloromethane to ensure melting. This solution was stirred for two hours under an inert argon atmosphere.

Figure 10:
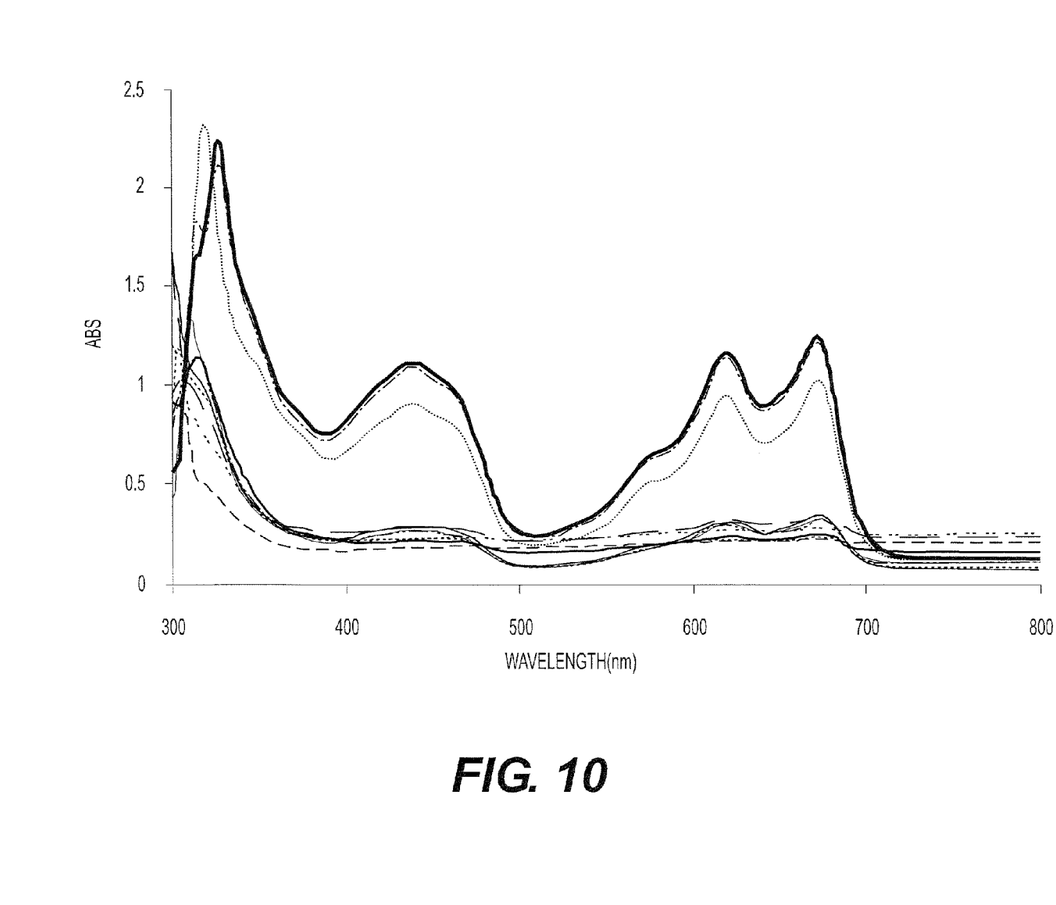
FIG. 10 is a graph showing the absorbance spectrum associated with the method of making palladium nanoparticles.

A sample of this solution was taken for electronic spectrum measurements of the palladium complex. The solution was divided into two parts: one part was placed in an ultraviolet-visible (UV-Vis) cell after dilution to a concentration of $1\times10^{-5}$ M, and the other part was held in an open flask. The two samples were exposed to the same dose of microwave radiation, and the sample absorbance was measured at regular intervals until the absorbance of the complex reached 0.2, as shown in FIG. 10.

All ligands (the diazo pigment and the acetic acid) associated with the metal palladium complex were digested and turned into volatile materials due to the temperature rise during microwave irradiation, which reduced $Pd^{+2}$ to $Pd^0$, leading to the formation of nano-palladium compounds in the form of a brown precipitate including palladium nanoparticles.

Figure 11:
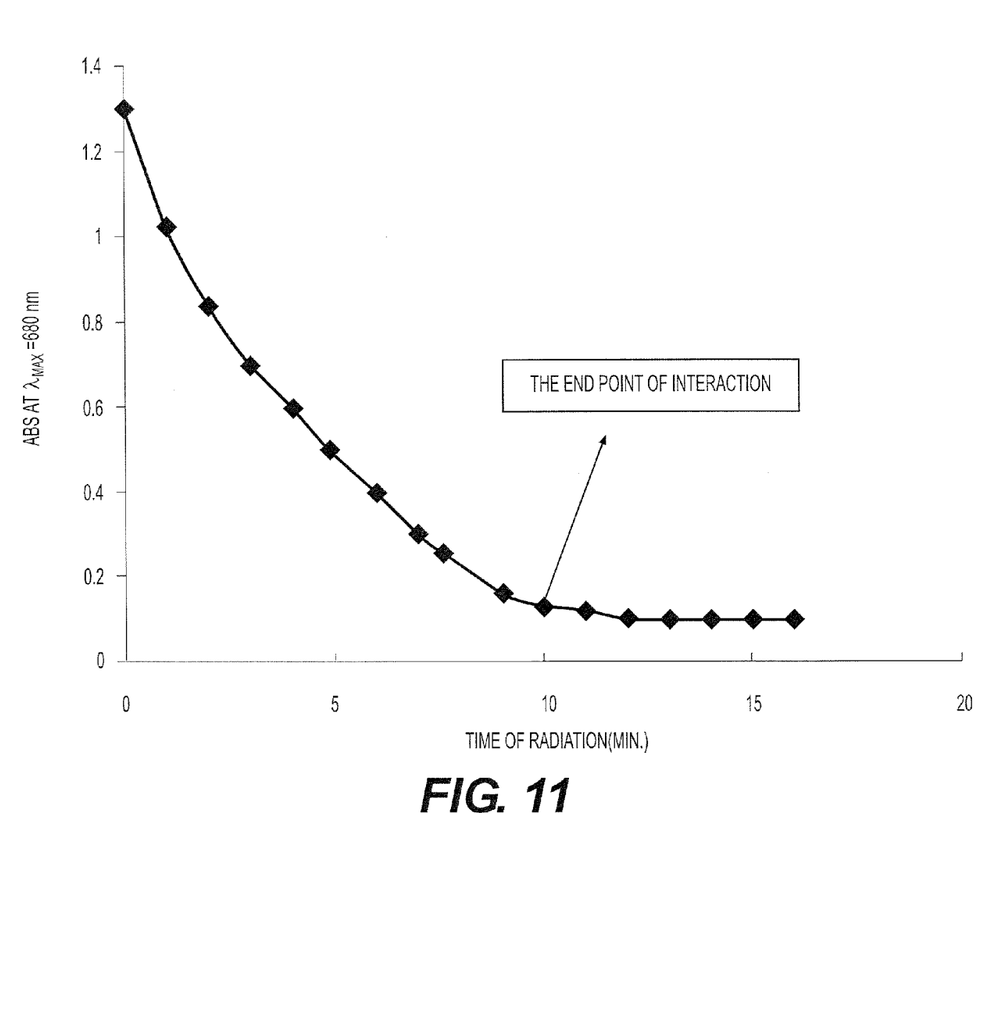
FIG. 11 is a plot of measured absorbance as a function of irradiation time associated with the method of making palladium nanoparticles.

In order to measure the speed of the microwave reaction and the time required to form granules of the palladium nanoparticles, the decrease in the absorbance of the complex at $\lambda_{max}$=680 nm with increasing radiation was used to measure the initial rate, and also to determine the time required for the reduction of the palladium(II) complex to $Pd^0$, with oleic acid as the reducing agent and microwave radiation as the source of thermal energy. FIG. 11 is a plot showing microwave absorbance (Abs) as a function of time. A natural decrease in absorbance with increasing exposure period to radiation can be clearly seen. Based on the plot of FIG. 11, 10 minutes of irradiation is sufficient to form the palladium nanoparticles, however, in order to ensure complete reaction, the sample was subjected to an additional 6 minutes of irradiation. The initial rate of reduction of $Pd^{+2}$ to $Pd^0$ was 0.127 mol/Ls.

In order to prepare the complex of palladium(II) acetate and the diazo pigment ligand, 0.053 g (0.236 mmol) of palladium(II) acetate was melted in a flask and then dissolved in about 20 mL of dichloromethane. This solution was kept at a temperature of 80° C. for 30 minutes under a flow of argon. The mixture was treated dropwise with 0.059 g (0.236 mmol) of the diazo pigment ligand dissolved in 20 mL of dichloromethane. This produced a dark green solution, visually confirming the complex of palladium(II) acetate and the diazo pigment ligand. The solution was reduced to almost 2 mL by vacuum evaporation and then treated by adding a sufficient amount of purified hexane to precipitate a spotted greenish-black solid. The precipitate was then washed with hexane several times. The product was dried under vacuum and stored in a desiccator.

Figure 1:
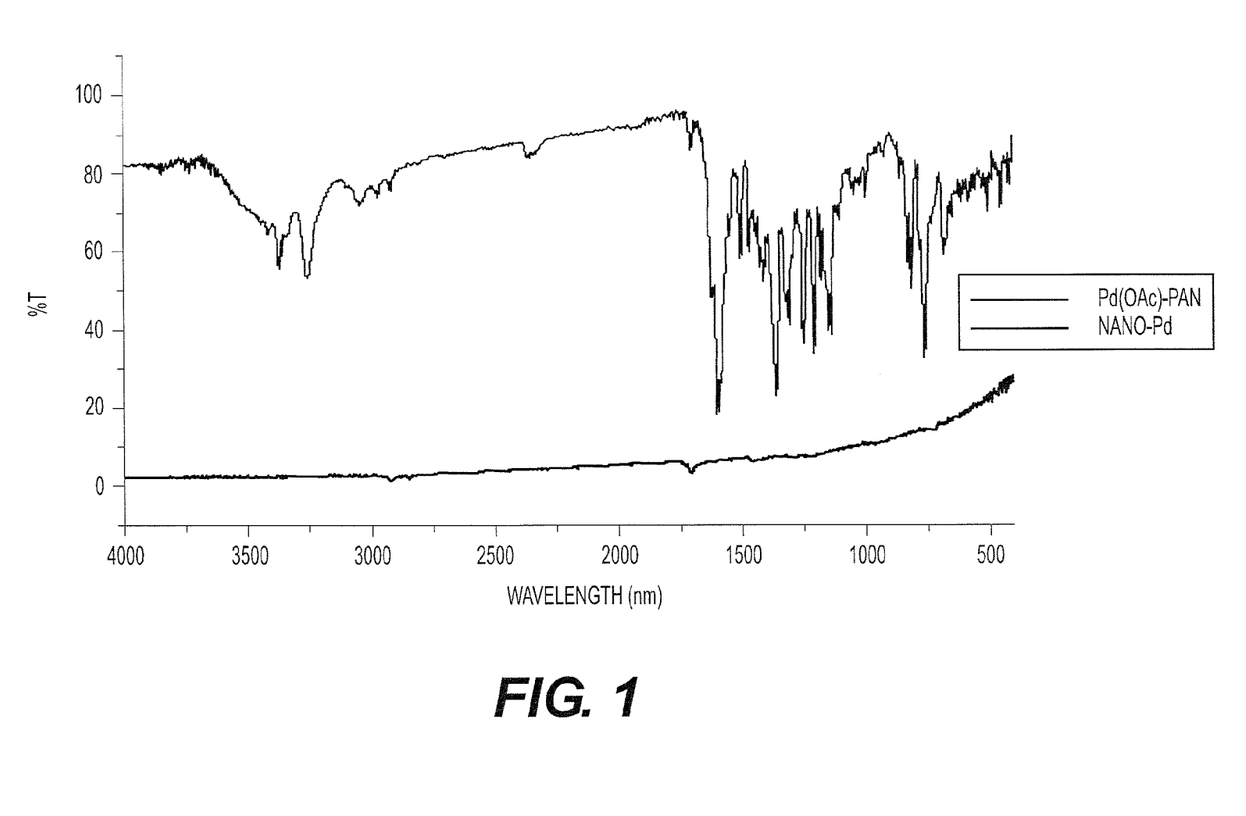
FIG. 1 is a graph showing Fourier transform infrared (FT-IR) spectrum results of a complex of palladium(II) acetate and a $C_{15}H_{11}N_3O$ ligand (Pd(OAc)-ligand) and palladium nanoparticles made by the method of making palladium nanoparticles.

FIG. 1 is a graph showing the infrared (IR) spectrum of both the complex of palladium(II) acetate and the diazo pigment ligand (Pd(OAc)-ligand) and the final palladium nanoparticle product (Nano-Pd). The spectrum for the palladium nanoparticles does not show the presence of any functional groups or PdO peaks, thus confirming that the product is in the form of pure palladium metal.

Figure 2:
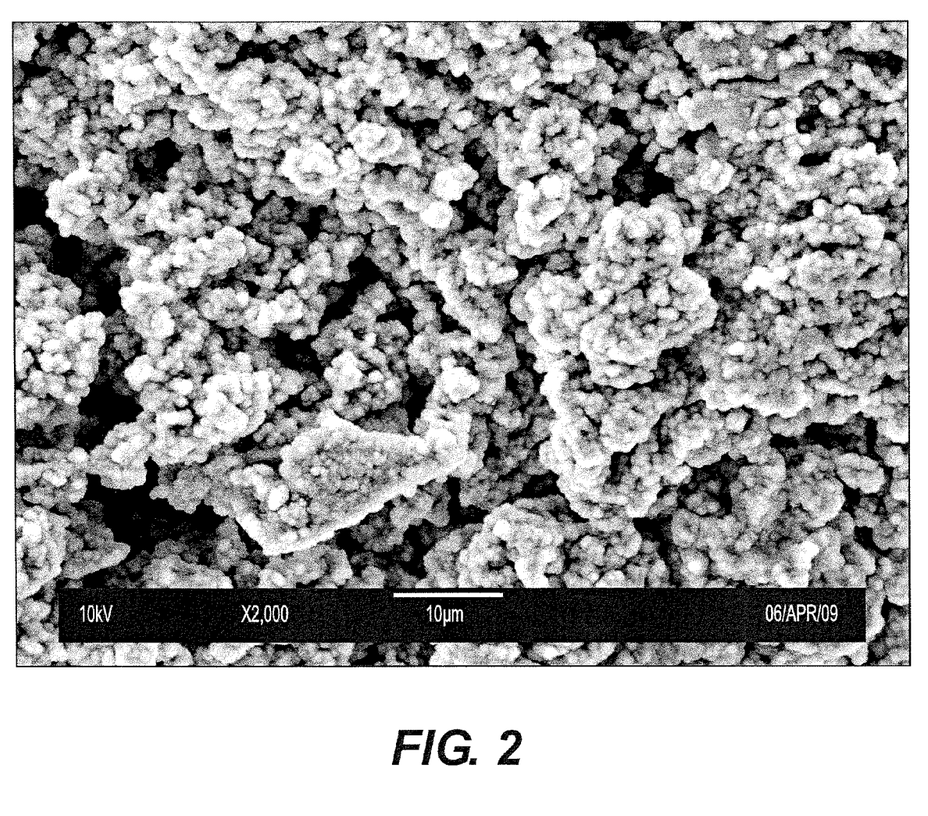
FIG. 2 is a scanning electron microscope (SEM) image of palladium nanoparticles made by the method of making palladium nanoparticles on a scale of 10 μm.
Figure 3:
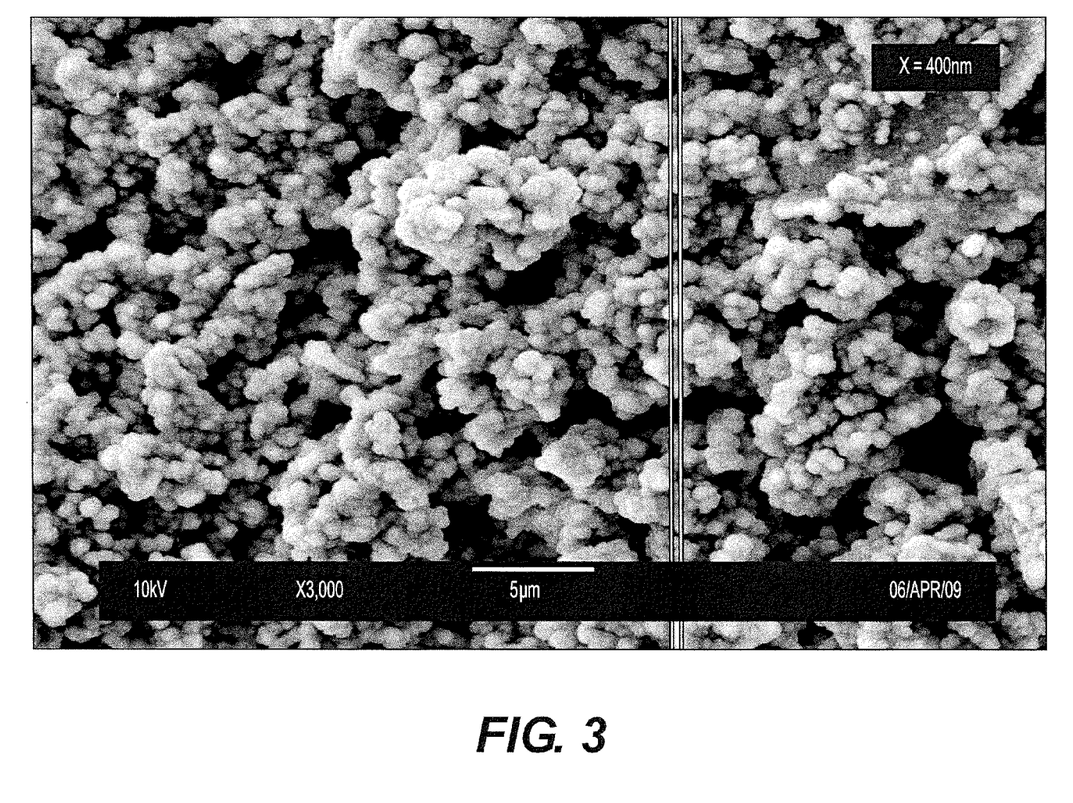
FIG. 3 is a scanning electron microscope (SEM) image of palladium nanoparticles made by the method of making palladium nanoparticles on a scale of 5 μm.
Figure 4:
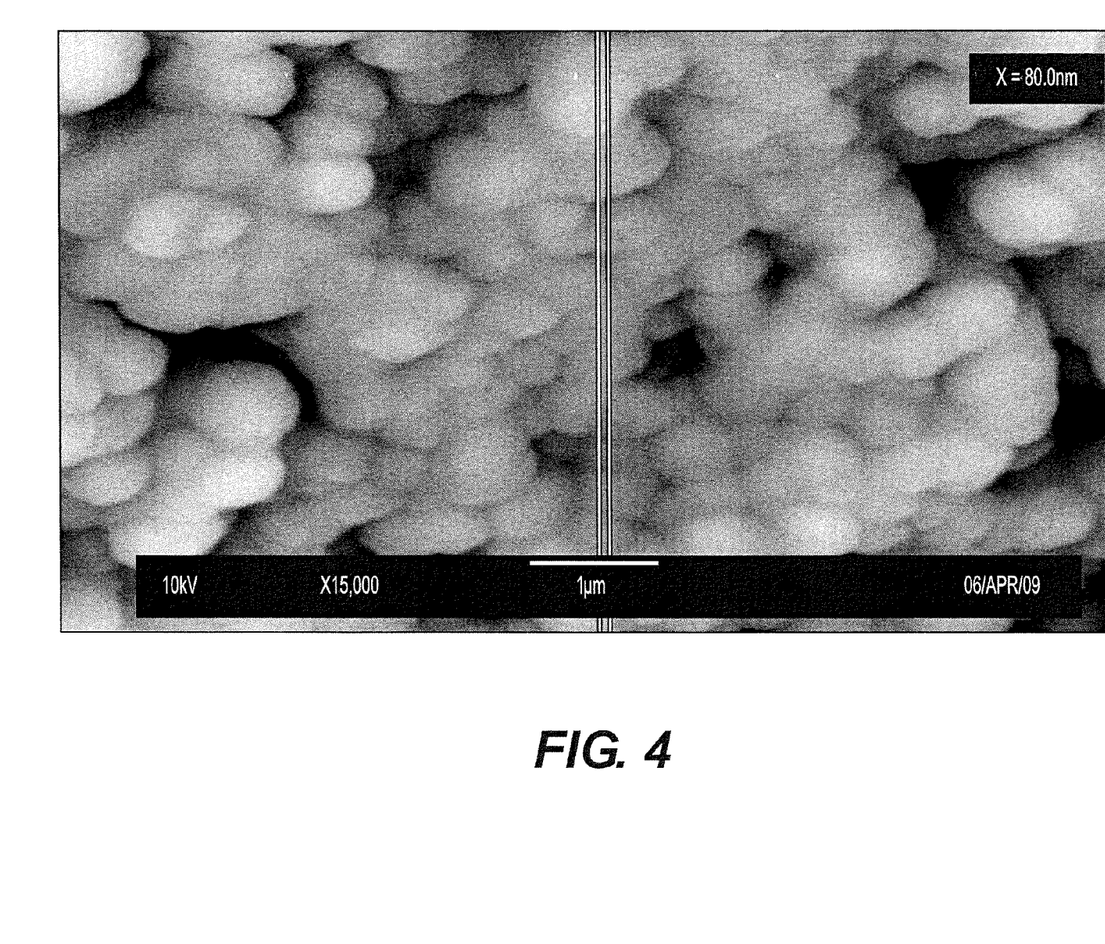
FIG. 4 is a scanning electron microscope (SEM) image of palladium nanoparticles made by the method of making palladium nanoparticles on a scale of 1 μm.
Figure 5:
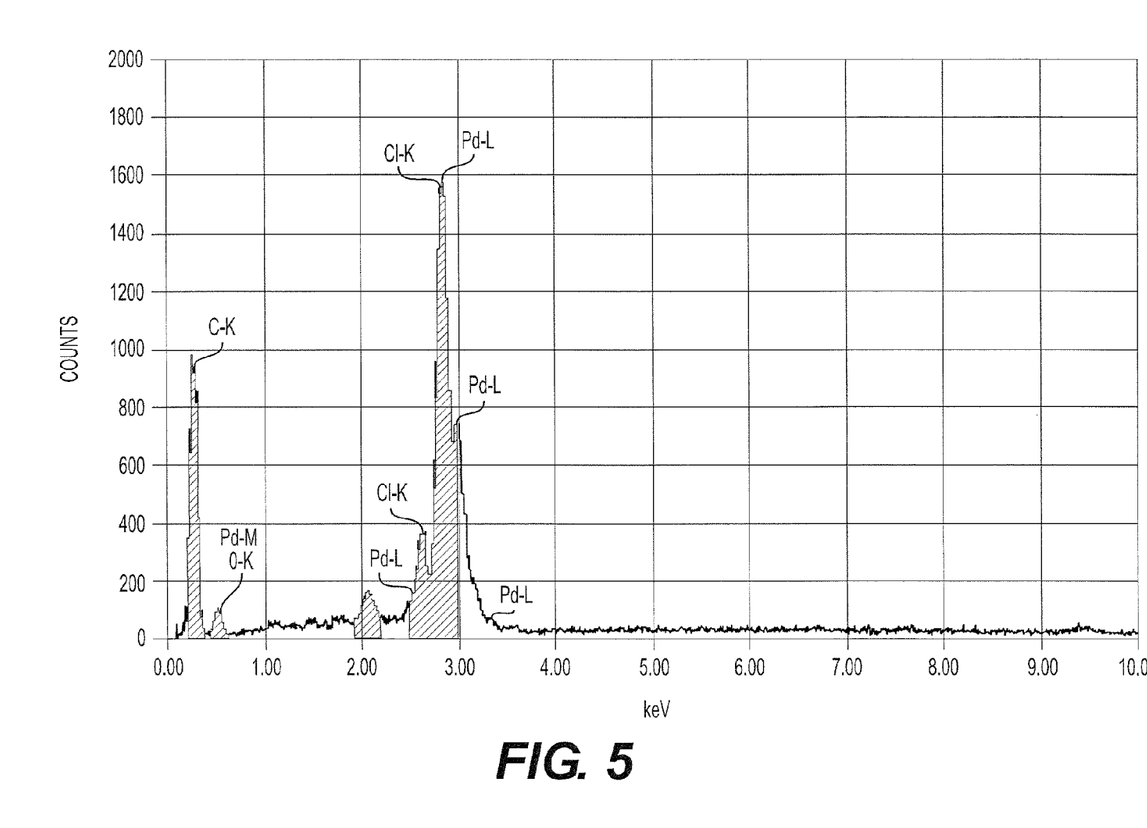
FIG. 5 is a graph showing the energy-dispersive X-ray spectroscopy (EDS) spectrum for the palladium nanoparticles made by the method of making palladium nanoparticles.
Figure 6A:
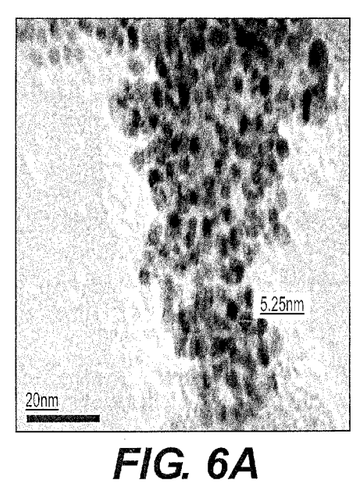
FIG. 6A is a transmission electron microscope (TEM) image of palladium nanoparticles made by the method of making palladium nanoparticles.
Figure 6B:
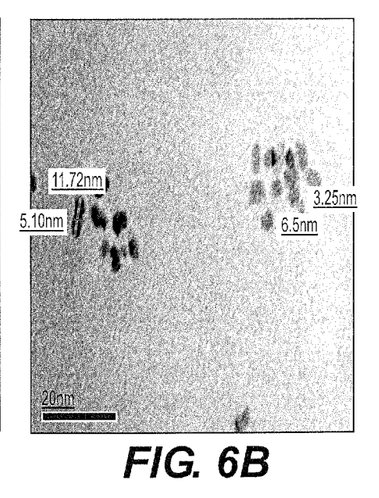
FIG. 6B is a transmission electron microscope (TEM) image of palladium nanoparticles made by the method of making palladium nanoparticles.
Figure 7A:
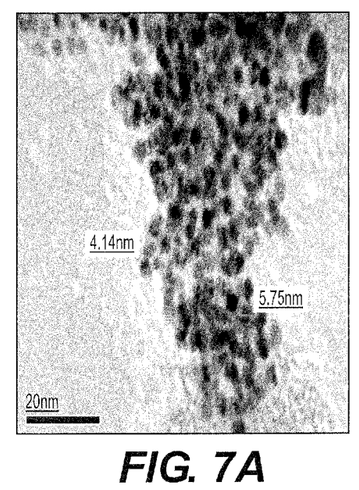
FIG. 7A is a transmission electron microscope (TEM) image of palladium nanoparticles made by the method of making palladium nanoparticles.
Figure 7B:
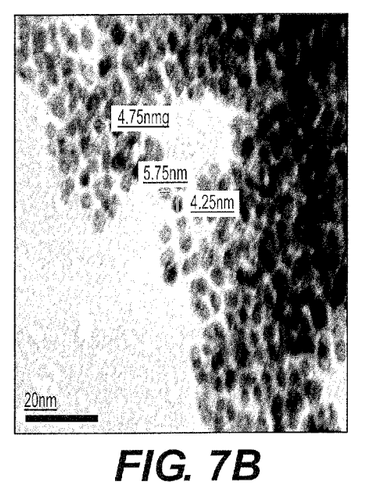
FIG. 7B is a transmission electron microscope (TEM) image of palladium nanoparticles made by the method of making palladium nanoparticles.

FIGS. 2, 3 and 4 are scanning electron microscope (SEM) images of the final palladium nanoparticle product on scales of 10 μm, 5 μm and 1 μm, respectively. In FIGS. 2, 3 and 4, coagulated, spherical Pd nanoparticles can be clearly seen. FIG. 5 is a graph showing the energy-dispersive X-ray spectroscopy (EDS) spectrum for the final palladium nanoparticle product. These results again confirm that no PdO nano metal is contained in the final product.

Figure 8:
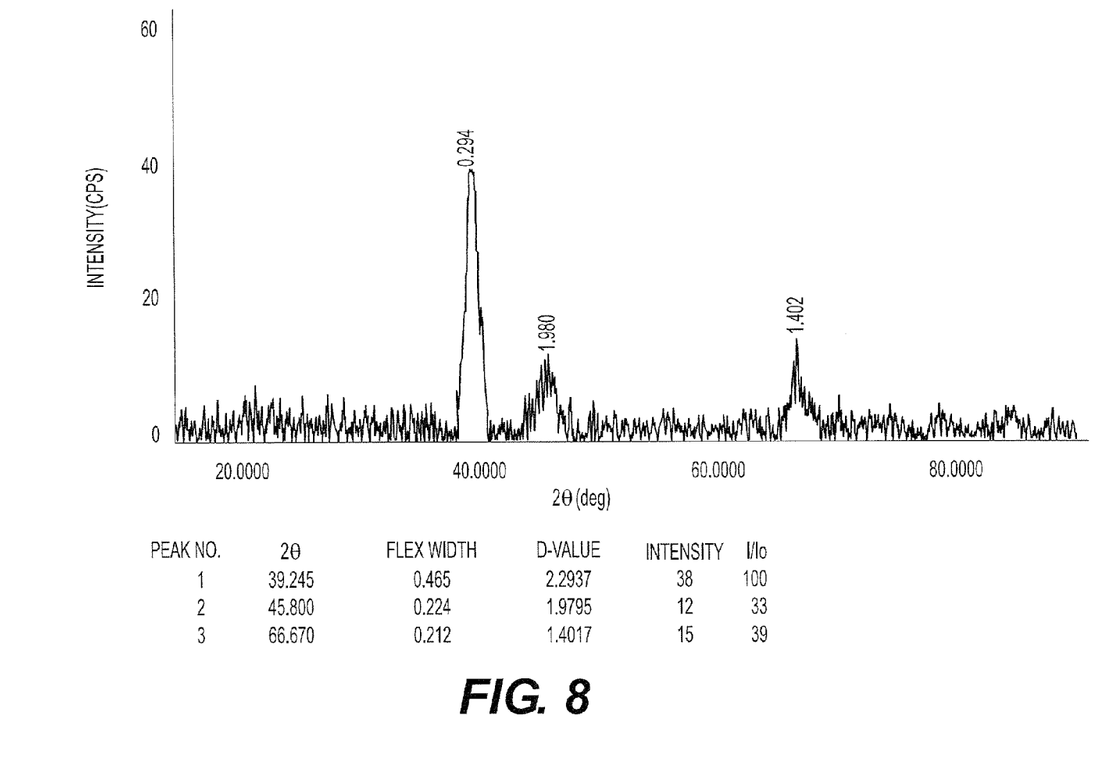
FIG. 8 is a graph showing the X-ray diffraction (XRD) results for the palladium nanoparticles made by the method of making palladium nanoparticles.

FIGS. 6A, 6B, 7A and 7B are each transmission electron microscope (TEM) images of the final palladium nanoparticle product, each shown at a scale of 20 nm. The palladium nanoparticles are clustered with a spherical shape. The size of the small-grained distals show all clusters with small diameters of about 6 nm to about 8 nm. FIG. 8 is a graph showing the X-ray diffraction (XRD) results for the final palladium nanoparticle product. It is not possible to note impurities in the extremely sharp signal of palladium that is nano-crystalline. Since the signals are consistent with palladium metal, it can be seen that the palladium peaks indicate the presence of a multi-crystalline product. Specifically, the crystalline form of nano-palladium gives 2θ reflections at 66.7, 45.8, and 39.5 for [220], [200] and [111], respectively. The Sherrer equation was used to calculate the size of the crystalline nano-sized particles from the measured 2θ values:

$$D = \frac{0.9\lambda}{\beta\cos\theta},$$

where D is the mean size of the ordered (crystalline) domains, which may be smaller or equal to the grain size, λ is the X-ray wavelength, β is the line broadening at half the maximum intensity (FWHM), after subtracting the instrumental line broadening, in radians, and θ is the Bragg angle (in degrees). The calculated value of D is found to be confined in the range of 2-10 nm, which is in agreement with the grain size as measured by TEM.

Figure 9:
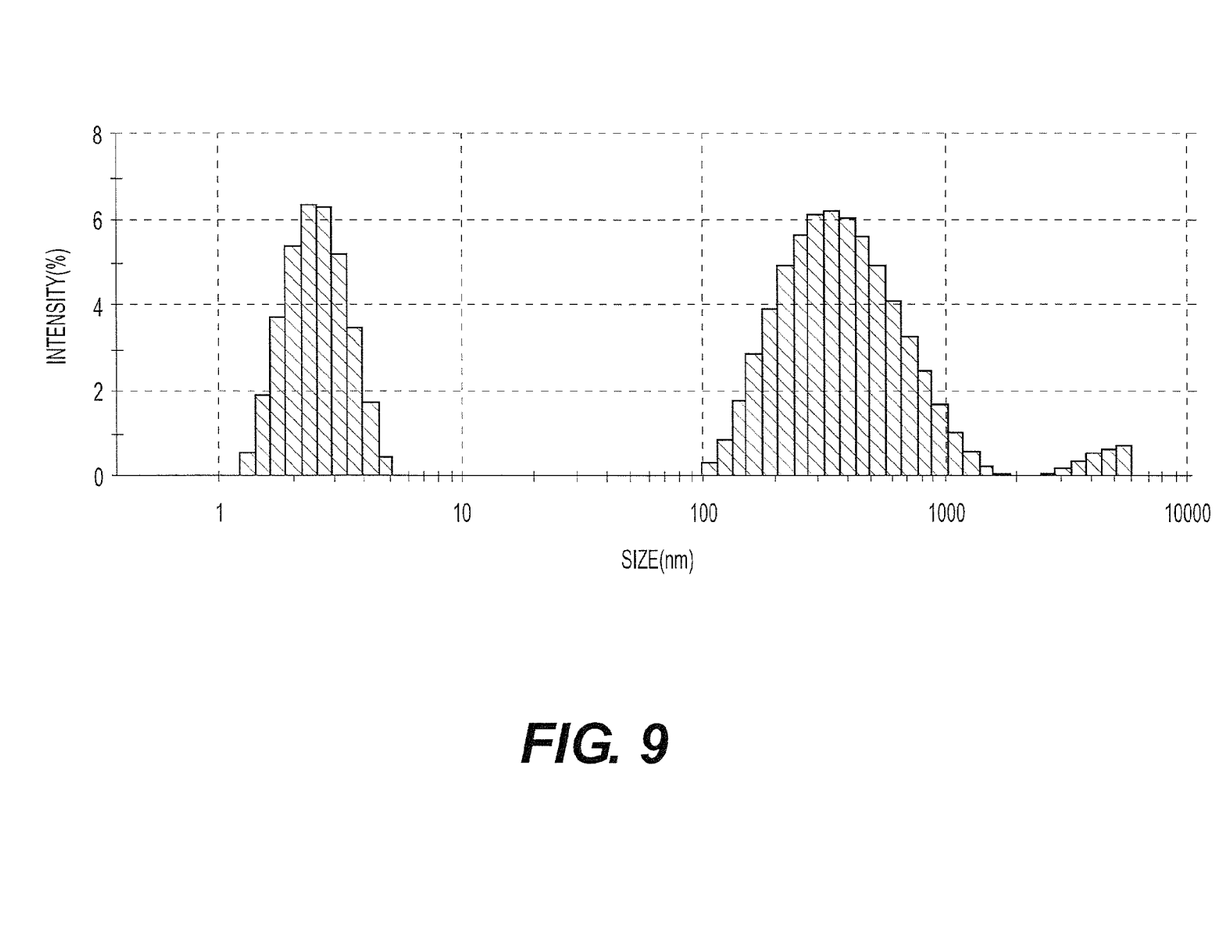
FIG. 9 is a plot showing size distribution by intensity of the palladium nanoparticles made by the method of making palladium nanoparticles.

The sample was analyzed using a nano-particle size analysis device. The sample to be analyzed was dispersed in a sufficient quantity of ethyl alcohol (EtOH). FIG. 9 is a plot showing size distribution of the final palladium nanoparticle product by intensity. The existence of two different sizes can be readily seen: a first cluster with a size of 2-7 nm, and a second cluster with a size of 100-800 nm. The first size is comparable with the XRD and TEM measurements. The second size that appears at 100-800 nm is the result of the original granules clustered together to become larger nano-sized palladium. This result is consistent with the SEM measurements.

The complex of palladium(II) acetate and the diazo pigment ligand and the final product of palladium nanoparticles (Pd-NPS) were screened as catalysts for Heck coupling reactions of iodobenzene with methyl acrylate to obtain the C—C corresponding product. The complex of palladium(II) acetate and the diazo pigment ligand and the final product of palladium nanoparticles (1-2 µmol), the iodobenzene (1.0 mmol), the methyl acrylate (1.16 mol), an appropriate base (KOH or $K_2CO_3$) (4 mmol) and an appropriate solvent (dimethylformamide) (10 mL) were added to a 100 mL Schlenk tube and the reaction mixture was subjected to a freeze-thaw cycle before it heated at 100° C. for 1-2 hours. During the coupling process, samples were taken from the reaction mixture using a syringe to control the conversion. The results are shown below in Table 1.

TABLE 1

Coupling Reaction with Iodobenzene and Methyl Acrylate

| Entry | Cat. (mg) | Solvent | Base | Temp (° C.) | Time (min) | Yield (%) |
|---|---|---|---|---|---|---|
| Complex or Pd-NPS | 0 | DMF | KOH | 100 | 100 | 0 |
| Complex | 4 | DMF | KOH | 100 | 60 | 60 |
| Pd-NPS | 4 | DMF | KOH | 100 | 60 | 99 |
| Complex | 4 | DMF | $K_2CO_3$ | 100 | 60 | 35 |
| Pd-NPS | 4 | DMF | $K_2CO_3$ | 100 | 60 | 88 |
| Complex | 4 | DMSO | KOH | 100 | 60 | 50 |
| Pd-NPS | 4 | DMSO | KOH | 100 | 60 | 92 |
| Complex | 2 | DMF | KOH | 120 | 60 | 50 |
| Pd-NPS | 2 | DMF | KOH | 120 | 60 | 90 |
| Pd-NPS | 1 | DMF | KOH | 120 | 100 | 99 |
| Pd-NPS | 4 | H2O | KOH | 100 | 100 | 60 |

In general, the complex and the Pd-NPS revealed high active catalysts under mid-Heck coupling reaction. The observed catalytic activities of Pd-NPS are 3-7 times higher than those of the corresponding complex. The base (KOH or $K_2CO_3$) is a critical material, acting as co-catalyst to activate both the complex and the Pd-NPS. The strong base (KOH) is found to have a better activation than the weak $K_2CO_3$. The best solvent was found to be dimethylformamide (DMF). An increase of the temperature enhanced the activities of the catalyst and allowed for a decrease of the amount of catalyst.

It is to be understood that the method of making palladium nanoparticles is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of making palladium nanoparticles, comprising the steps of:

melting a complex of palladium(II) acetate and a ligand to form a solution, wherein the ligand comprises 1-(pyridin-2-yldiazenyl)naphthalen-2-ol, wherein the melting comprises the steps of:

a) melting a volume of palladium(II) acetate;

b) dissolving the melted volume of palladium(II) acetate in oleic acid and dichloromethane to form a palladium-dichloromethane solution;

c) dissolving the ligand in oleic acid and dichloromethane to form a ligand-dichloromethane solution;

d) adding the ligand-dichloromethane solution to the palladium-dichloromethane solution to yield a precursor solution;

e) reducing the precursor solution under vacuum; and f) adding hexane to the reduced precursor solution to precipitate the complex of the palladium(II) acetate and the ligand out of the reduced precursor solution;

stirring the solution under an inert atmosphere, wherein the step of stirring the solution under the inert atmosphere comprises stirring the solution for about two hours under an argon atmosphere; and irradiating the solution with microwave radiation for about 10 minutes to about 16 minutes to produce palladium nanoparticles having a diameter of about 2 nm to about 10 nm.

2. The method of making palladium nanoparticles as recited in claim 1, wherein the palladium nanoparticles have a diameter of about 4.1 nm to about 5.75 nm.

3. The method of making palladium nanoparticles as recited in claim 1, wherein the palladium nanoparticles have a diameter of about 6 nm to about 8 nm.

* * * * *